United States Patent
Woelfel (10) Patent No.: US 9,238,118 B2
(45) Date of Patent: Jan. 19, 2016

(54) MULTIPLE LUMEN HOSE

(75) Inventor: Mark Edward Woelfel, Oakridge, NJ (US)

(73) Assignee: CAREFUSION CORPORATION, San Diego, CA (US)

( * ) Notice: Subject to any disclaimer, the term of this patent is extended or adjusted under 35 U.S.C. 154(b) by 552 days.

(21) Appl. No.: 13/596,453

(22) Filed: Aug. 28, 2012

(65) Prior Publication Data

US 2014/0060530 A1    Mar. 6, 2014

(51) Int. Cl.
*F16L 11/22*    (2006.01)
*A61M 16/08*    (2006.01)
*F16L 11/15*    (2006.01)

(52) U.S. Cl.
CPC ............ *A61M 16/0875* (2013.01); *F16L 11/15* (2013.01); *F16L 11/22* (2013.01); *A61M 2207/10* (2013.01)

(58) Field of Classification Search
CPC .............. F16L 9/18; F16L 9/19; F16L 11/15; F16L 11/22
USPC .......................... 138/116, 117, 121, 115, 173
See application file for complete search history.

(56) References Cited

U.S. PATENT DOCUMENTS

| | | | |
|---|---|---|---|
| 388,824 A * | 9/1888 | Callan ........................... | 138/115 |
| 388,867 A * | 9/1888 | Hayden ......................... | 138/115 |
| 3,286,305 A | 11/1966 | Seckel | |
| 3,578,777 A * | 5/1971 | DeGain ......................... | 138/121 |
| 3,885,820 A * | 5/1975 | Trumbull et al. .......... | 285/124.5 |
| 4,096,887 A | 6/1978 | Streit | |
| 4,132,576 A | 1/1979 | Neroni et al. | |
| 4,654,962 A | 4/1987 | Ben-Dov | |
| 5,121,746 A | 6/1992 | Sikora | |
| 5,305,797 A | 4/1994 | Roy, Sr. | |
| 5,360,291 A | 11/1994 | Shimizu | |
| D405,522 S | 2/1999 | Hoenig et al. | |
| 5,996,639 A | 12/1999 | Gans et al. | |
| D424,687 S | 5/2000 | Hoenig et al. | |
| 6,394,142 B1 | 5/2002 | Woelfel et al. | |
| 6,415,793 B1 | 7/2002 | Kretz | |
| 6,431,218 B1 | 8/2002 | Woelfel et al. | |
| 6,450,205 B1 | 9/2002 | Check | |
| 8,809,687 B2 * | 8/2014 | Watanabe ..................... | 174/254 |
| 2002/0036019 A1 | 3/2002 | Woelfel et al. | |

OTHER PUBLICATIONS

"Adult Anesthesia Breathing Circuit", Products—Anesthesia—Vital Signs Inc., http://vital-signs.gehealthcare.com, Oct. 20, 2011.

* cited by examiner

Primary Examiner — Kevin P Shaver
Assistant Examiner — Robert Nichols, II
(74) Attorney, Agent, or Firm — McDermott Will & Emery LLP (57) ABSTRACT

A multiple lumen hose includes a generally circumferential base wall. A plurality of corrugations extend radially outward from the base wall. A septum is disposed interior to the base wall such as to divide the interior of the base wall into at least a first lumen and a second lumen. A first scallop extends outward from the circumferential base wall between adjacent corrugations. A second scallop extends outward from the circumferential base wall between adjacent corrugations.

10 Claims, 7 Drawing Sheets

MULTIPLE LUMEN HOSE

BACKGROUND

The present disclosure relates to fluid or gas conveyance. More specifically, the present disclosure relates to a hose with multiple lumen for fluid or gas conveyance having at least one inner planar partition dividing hose into a plurality of lumen.

Multiple lumen hoses are used in various medical, commercial, and industrial applications for fluid and gas conveyance. In many of these applications, an outer wall of the hose is corrugated in order to provide the hose with greater flexibility and kink resistance.

One example of such application of a multiple lumen hose is the medical field, particularly for ventilatory assistance and/or anesthesia delivery. During anesthesia delivery a multiple lumen hose can be used in a breathing circuit to convey oxygen or oxygen enriched gas from a ventilator to a patient connection such as a mask or endotracheal tube by one lumen and to remove the exhaled gases from the patient back to the anesthesia machine or ventilator for gas scavenging, remedial treatment and/or recirculation back to the patient.

BRIEF DISCLOSURE

An exemplary embodiment of a multiple lumen hose includes a generally circumferential base wall defining an interior. A plurality of corrugations extend radially outward from the base wall. A septum is disposed interior to the base wall such as to divide the interior of the base wall into at least a first lumen and a second lumen. The septum is secured to the circumferential base wall. A first scallop extends outward from the circumferential base wall between adjacent correlations in a localized area about the septum and the septum is secured to the first scallop. A second scallop extends outward from the circumferential base wall between adjacent corrugations in a localized area about the septum. The septum is secured to the second scallop and the second scallop is opposite the first scallop.

An exemplary embodiment of a method of manufacturing a dual lumen conduit includes providing at least one mold comprising a plurality of depressions for forming a plurality of corrugations, a plurality of ridges for forming a plurality of uncorrugated regions, and a plurality of cavities through the ridges for forming a plurality of scallops in the uncorrugated regions between the corrugations. An extrusion comprising a circumferential base wall and a septum interior to the circumferential base wall is placed in contact with the at least one mold. The differential pressure is provided across the base wall. The pressure within the extrusion is greater than the pressure between the base wall and the mold. A plurality of corrugations are formed in the base wall. A plurality of scallops are formed in the base wall in the uncorrugated region. The scallops are aligned about the septum.

An exemplary embodiment of a dual lumen breathing circuit tube includes a generally circumferential base wall defining a conduit. The base wall extends between a first end cuff and a second end cuff. A plurality of corrugations extend radially outward from the base wall. A plurality of second scallops extend outward from the circumferential base wall between adjacent corrugations. Each second scallop of the plurality is opposite a first scallop. A septum is disposed interior of the base wall, scallop, and corrugations. The septum is secured to the corrugations, first scallops, and second scallops. The septum divides the conduit into a first lumen and a second lumen.

DETAILED DISCLOSURE

Figure 1:
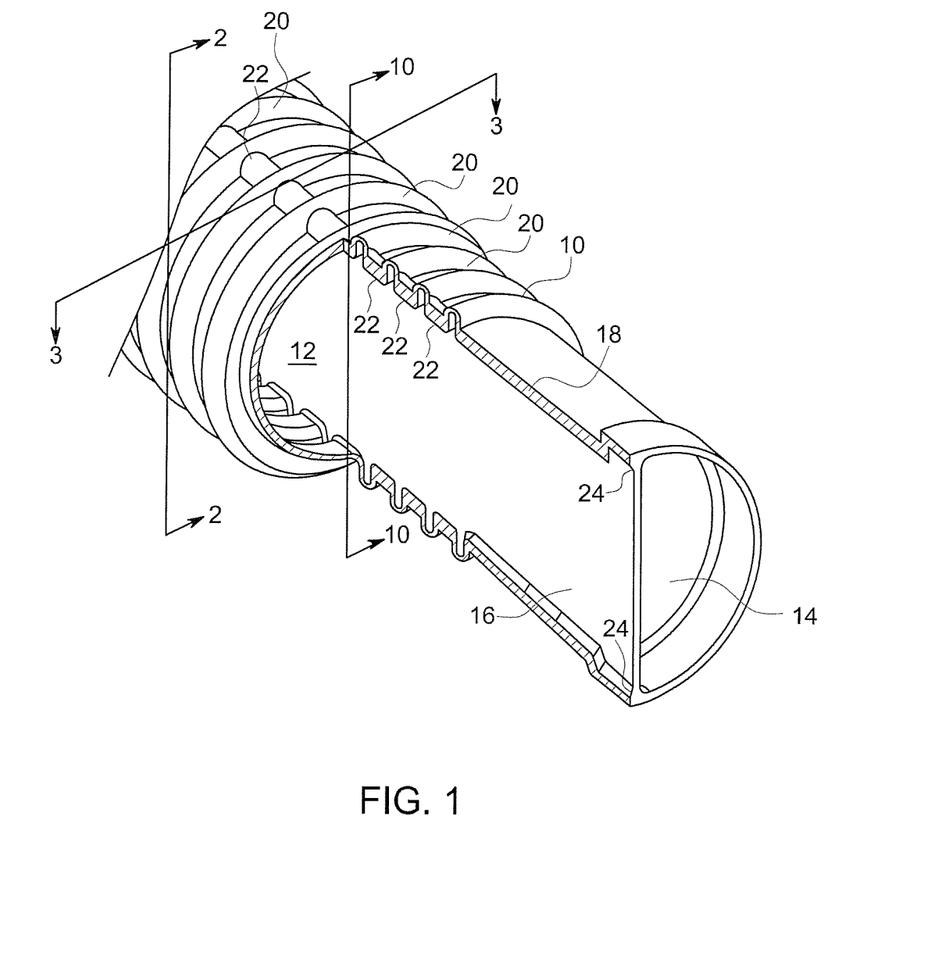
FIG. 1 is a sectional view of an embodiment of a multiple lumen hose.

FIG. 1 depicts a partial sectional view of an embodiment of a multiple lumen hose 10. In the embodiment of the multiple lumen hose 10 depicted in FIG. 1, the multiple lumen hose 10 is a dual lumen hose having a first lumen 12 and a second lumen 14 separated by a septum 16 as will be described in further detail herein. Therefore, while the multiple lumen hose 10 will generally be referred to as a dual lumen hose with reference to the depicted embodiment, it is to be understood that the multiple lumen hose as disclosed herein may comprise more than two lumens.

The multiple lumen hose 10 includes a base wall 18. A plurality of corrugations 20 extend radially outward from the base wall 18 such that the hose 10 is corrugated along at least a substantial portion of its length. The septum 16 extends between an interior diameter of the base wall 18 and in a process as disclosed herein, the septum 16 is locally stretched as the corrugations 20 are formed in the base wall 18 such that the septum 16 extends out to the inside diameter of the corrugations 20 as well.

It has been recognized by the applicant that the localized stretching in the formation of the corrugations 20 causes weaknesses in the corrugations 20 at the region of the intersection 24 between the septum 16 and the corrugations 20 that experiences the localized stretching. These weaknesses can develop into cracks or holes through the outside wall in the corrugations 20 during the course of use of the hose 10. This can cause leading of oxygenated or anesthetic entrained gases away from the patient in the medical setting. When such a condition is detected, the hose 10 must be replaced.

As disclosed herein, a solution to the localized weaknesses in the corrugations 20 is provided by a series of scallops 22 arranged in the base wall 18 at an area about an intersection 24 between the septum 16 and the base wall 18. As can be seen in FIG. 1, in an embodiment, a corresponding pair of scallops 22 of the series are aligned on opposed sides of the septum 16.

As will be described in further detail herein, the scallops serve to reduce the localized stretching, resulting in a stronger and more durable corrugations 20, particularly along the intersection 24 between the septum 16 and the corrugations 20. It has further been observed that in embodiments, the reduced localized stretching further results in a more even septum surface, which in embodiments can have the effect of reducing fluid resistance through the multiple lumen hose.

Some embodiments of the multiple lumen hose 10 as disclosed above can be used in the medical field such as in patient respiratory assistance and anesthesia delivery. In such embodiments, the hose 10 extends between cuffs 36 at the ends of the hose 10 that are formed into the base wall 18 such as to create suitable connectors to engage other breathing circuit components or medical devices.

Figure 2:
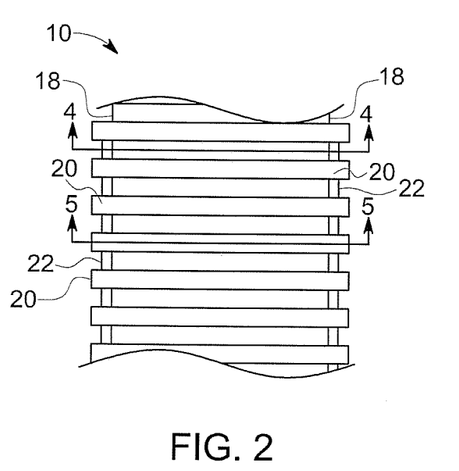
FIG. 2 is a side view of the embodiment of the multiple lumen hose of FIG. 1 taken in the direction of line 2-2.
Figure 3:
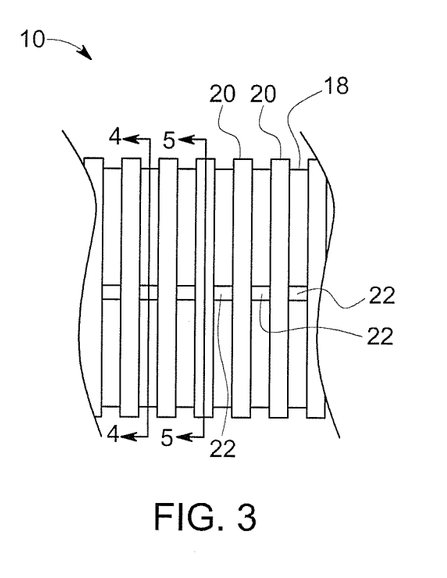
FIG. 3 is a top view of the embodiment of the multiple lumen hose depicted in FIG. 1 as viewed from line 3-3.

FIGS. 2 and 3 respectively depict side and top views of an embodiment of the multiple lumen hose 10 depicted in FIG. 1 as viewed in the direction of lines 2-2 and 3-3 in FIG. 1. Referring first to FIG. 3, the scallops 22 are depicted between each of the corrugations 20. As also shown in FIG. 3, each of the scallops 22 is associated with the regions of the hose 10 between adjacent corrugations 20. While it is not intended to be limiting on the scope of the scallops contemplated by the present disclosure, the scallops 22 are of a small dimension as compared to that of the base wall 18 and the corrugations 20. Therefore, in embodiments, the scallops are localized to a region about the intersection 24 of the base wall 18 and the septum 16.

Referring now to the side view of the multiple lumen hose 10 depicted in FIG. 2, it can be seen that the scallops 22 extend in a direction towards the corrugations 20 radially past the base wall 18, yet stop short of the corrugations 20. While depicted as stopping short of the corrugations 20 in the embodiment depicted in FIG. 2, it is to be understood that in alternative embodiments, the scallops 22 need not be so limited. Therefore, it is contemplated that in an embodiment, the scallops 22 may extend out to the same extent as the corrugations 20. In still further embodiments, the scallops 22 extend at some distance greater than that of the base wall 18, but less than that of the corrugation 20. As a non-limiting example, the radial distance between similar points (e.g. inside or outside surfaces) of the scallop 22 and that of the corrugation 20 may be between 40% and 60% of the radial distance between similar points on the base wall 18 and the corrugation 20.

Figure 4:
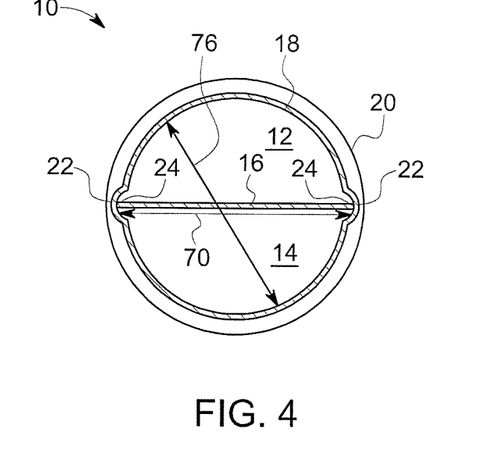
FIG. 4 is a cross sectional view of an embodiment of a multiple lumen hose as taken along line 4-4 in FIGS. 2 and 3.
Figure 5:
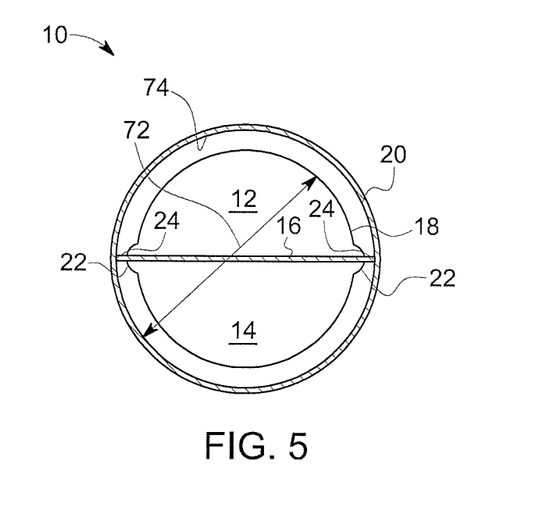
FIG. 5 is a cross sectional view of an embodiment of a multiple lumen hose as taken along line 5-5 in FIGS. 2 and 3.

FIG. 4 is a cross sectional view of an embodiment of the multiple lumen hose 10 as taken along line 4-4 which appears in FIGS. 2 and 3. The cross section depicted in FIG. 4 is taken through a portion of the multiple lumen hose 10 that includes scallops 22. Therefore, the scallops 22 appear in cross section. FIG. 5 is a cross sectional view of an embodiment of a multiple lumen hose 10 taken along lines 5-5 appearing in FIGS. 2 and 3. FIG. 5 is a cross sectional view taken through a portion of the multiple lumen hose 10 that includes a corrugation 20. Therefore, the corrugation 20 appears in cross section. By comparing FIGS. 4 and 5, it can be seen that much of the cross section appears similar to that as previously known in the art in corrugated multiple lumen hose. However, the scallops 22 can be clearly seen in FIGS. 4 and 5 at an area about the intersection 24 between the septum 16 and either the scallops 22 or corrugation 20. Further by comparing FIG. 4 to FIG. 5, it can be seen that in order to extend the septum 16 out to the corrugation 20, the septum 16 must be stretched from an inside diameter 70 between the scallops 22 out to an inside diameter 72 between the interior edges 74 of the corrugation 20. In embodiments, the inside diameter 70 will be greater than an inside diameter 76 of the circumferential base wall 18 while being less than inside diameter 72. As discussed above, the scallops 22 in the base wall 18, particularly as shown in FIG. 4, reduces the local distance that the septum 16 and the base wall 18 must be stretched in order to extend out to the corrugation 20, as shown in FIG. 5.

FIGS. 4 and 5 depict the scallops to be rounded or otherwise curved in cross section; however, this is not intended to be limiting on the scope of the shape of the scallops and it is contemplated within this disclosure. The scallops 22 can be of other cross sectional shapes, including, but not limited to triangular, rectangular, or trapezoidal. In still further embodiments wherein the scallops 22 are rounded, the scallops could exemplarily be elliptical of U-shaped.

Figure 11:
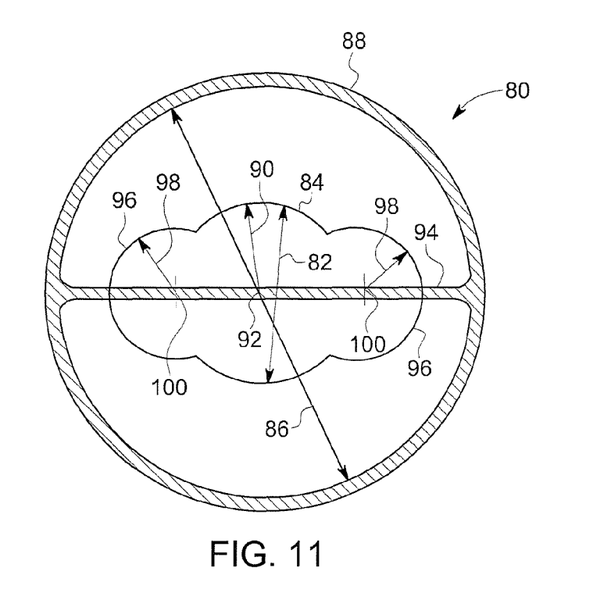
FIG. 11 is a cross sectional view of an alternative embodiment of a multiple lumen hose as disclosed herein.

In exemplary embodiments, the scallops 22 are centered along the septum 16, particularly in that the scallops 22 circumferentially extend about the intersection 24 of the septum 16 with the base wall 18. However, other positional relationships between the septum and the scallops are contemplated. In embodiments, the scallops are generally dimensioned to only be in a local area bout the septum. FIG. 11 depicts an alternative embodiment with larger radiused scallops. In embodiments with generally smaller dimensional scallops, the flexibility of the corrugated hose is generally maintained compared to a multiple lumen corrugated hose without scallops.

Figure 6:
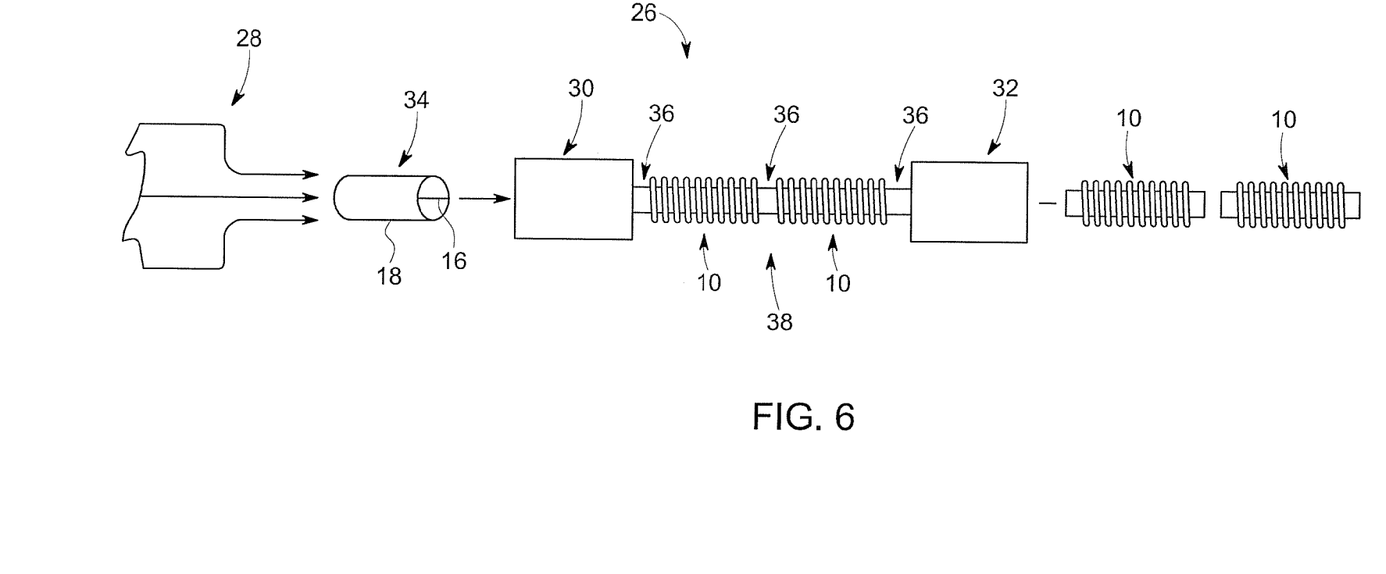
FIG. 6 is a diagrammatical illustration of a method and apparatus for manufacturing a multiple lumen hose in accordance with an embodiment.

FIG. 6 is a diagrammatical illustration of exemplary embodiments of a method and apparatus for manufacturing a multiple lumen hose as described herein. The apparatus 26 includes a co-extruder 28, a corrugator 30, and a cutter 32. The co-extruder 28 may be any of a variety of co-extruders that can co-extrude a hollow cylindrical base wall from a first plastic material and can co-extrude a planar, or substantially planar, inner septum from a second plastic material and which the two co-extrusions unite to form an integral co-extrusion 34, or what is sometimes referred to in the art as a parison. In an embodiment of the co-extrusion 34, the base wall 18 is extruded from a first plastic material and the septum 16 is extruded from a second plastic material with the plastic materials uniting, fusing, and melting together to produce an integral co-extrusion 34. While the co-extrusion 34 has been described above as being constructed of components of different materials, it is understood that in alternative embodiments both the base wall 18 and the septum 16 can be constructed of the same material. As a still further example, the base wall 18 can be constructed of a blend of about 91% polyethylene and about 9% EVA, causing such base wall 18 to be at least substantially transparent, and that the septum 16 may be co-extruded from a suitable blend of plastic material which by non-limiting example may be a blend of about 81% polyethylene, about 1% EVA containing a blue colorant, and about 18% EVA causing the septum 16 to be colored blue. It is still further understood that while the blue coloring has been disclosed, any other such optically perceptible color may be used in the construction of the septum 16.

The integral co-extrusion 34 is fed continuously into the corrugator 30. The corrugator 30 continuously corrugates the base wall 18 of the integral co-extrusion 34. The corrugator 30 may also operate to produce cuffs 36 at predetermined spaced locations to provide opposed ends of the multiple lumen hose 10 after the corrugated integral co-extrusion 38 has been cut into the multiple lumen hose 10 by the cutter 32. The integral corrugated co-extrusion 38 is fed continuously into a cutter 32 that is suitable for cutting plastic products that pass continuously therethrough. The cutter 32 cuts the corrugated integral co-extrusion 38 into discrete multiple lumen hoses 10.

Figure 7:
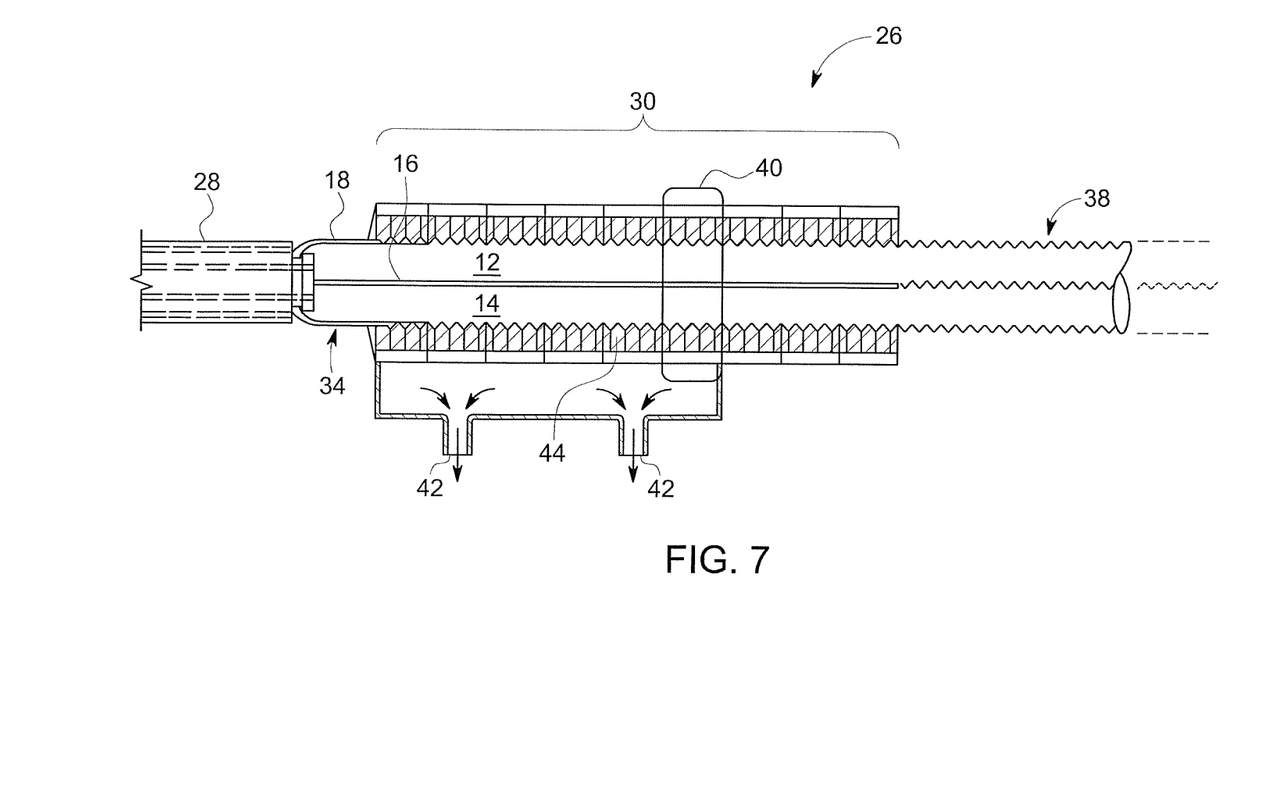
FIG. 7 is an illustration of an embodiment of a vacuum assisted blow molding apparatus as used to construct an exemplary embodiment of a multiple lumen hose.

FIG. 7 is an alternative depiction of an exemplary embodiment of the apparatus 26 for constructing the multiple lumen hose 10 as disclosed herein. The apparatus 26 includes the co-extruder 28 that produces an integral co-extrusion 34 that includes a base wall 18 and a septum 16, as described above. The corrugator 30 is shown in greater detail as compared to FIG. 6. The corrugator 30 shapes the base wall 18 and, in part, the septum 16, as disclosed herein in order to corrugate the base wall 18 of the integral co-extrusion 34 to form the multiple lumen hose 10. The corrugator 30 provides either a positive or a negative pressure about the first lumen 12 and second lumen 14. In one embodiment, air is injected into the lumens 12 and 14. The injected air creates a positive pressure within both of the lumens 12 and 14 which forces the base wall 18 into the series of corrugated molds exemplarily identified as mold 40 within the corrugator 30. Alternatively, as depicted in FIG. 7, vacuum assisted blow molding may also be used. In vacuum assisted blow molding, vacuum inlets 42 outside the molds 40 and vacuum slots 44 operate in tandem to create a negative pressure outside of lumens 12 and 14 to pull the base wall 18 against the corrugated molds 40 of the corrugator 30. While the above techniques and apparatus for producing corrugations in an integral co-extrusion 34 have been herein explicitly described, it will be recognized that alternative techniques or apparatus may also be used to corrugate the integral co-extrusion 34 in the manner as disclosed herein.

Figure 8:
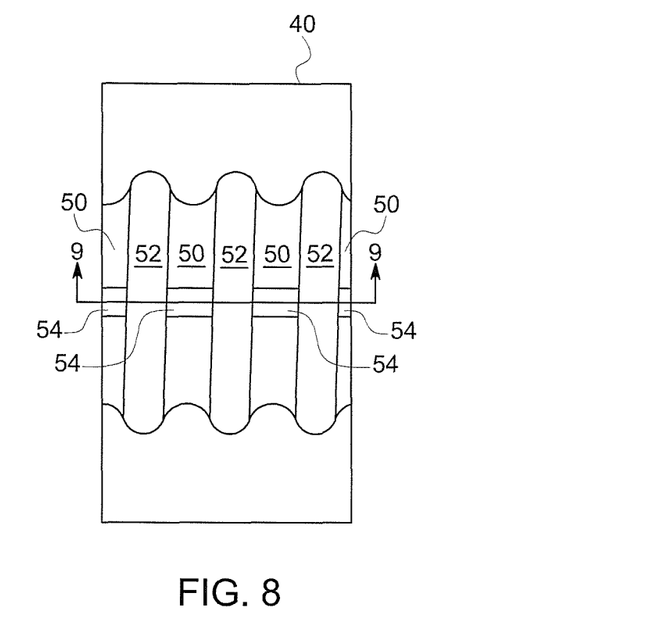
FIG. 8 is a cross sectional view of an embodiment of a mold as may be used to construct an embodiment of a multiple lumen hose.

FIG. 8 is a more detailed view of an embodiment of a mold 40 as depicted above in FIG. 7. It is to be noted that the mold 40 forms one-half of a matching pair of mold halves, exemplarily depicted in FIG. 9 as first mold half 46 and second mold half 48. Referring back to FIG. 8, the mold 40 includes a plurality of ridges 50 and depressions 52. It is to be noted that the mold 40 is negative impression of the corrugations to be formed. Therefore, when pressure is applied to the integral co-extrusion as described above, the portions of the base wall that are drawn into the depressions 52 become the corrugations in the base wall, while the ridges 50 generally maintain the original outside dimension of the integral co-extrusion. It is to be noted that in some embodiments, the ridges 50 are also of a greater diameter through the mold 40 such that during the manufacturing process, the base wall 18 is drawn outward to engage the ridges as well.

The mold 40 further includes cavities 54 cut into the ridges 50. When the base wall 18 is drawn into the cavities 54, the scallops in the multiple lumen hose as described herein are formed. In one embodiment, the cavities 54 may be cut into the ridges 50 with a ball end mill, while in other embodiments, the mold is cast such as to achieve a similar mold design. It is to be noted that the septum 16 in the integral co-extrusion is to be in alignment with the cavities 54, thus the integral co-extrusion 34 is oriented with the mold 40, such that the septum 16 of the integral co-extrusion is perpendicular to the orientations of the mold 40.

Figure 9:
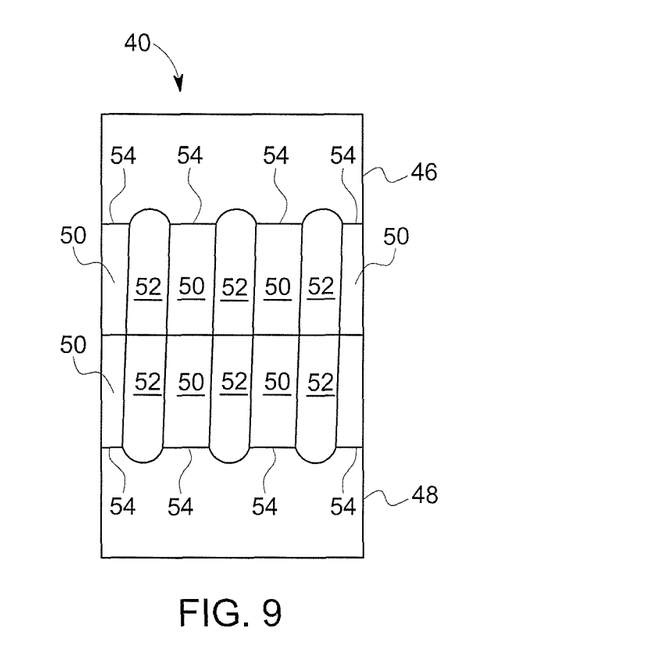
FIG. 9 is a cross sectional view of an embodiment of a mold used to construct an embodiment of a multiple lumen hose as taken along line 9-9 in FIG. 8.

FIG. 9 provides an alternative view of the mold 40 taken along line 9-9 in FIG. 8. As mentioned above, the mold 40 includes matching first mold half 46 and second mold half 48 in order to form a complete mold 40. The view of the mold 40 is taken in a plane that is parallel in orientation to that of the septum 16 of the integral co-extrusion 34 as it passes through the mold 40. Thus, an alternative view is provided of the ridges 50, depressions 52, and cavities 54 found in the first mold half 46 and the second mold half 48.

Figure 10:
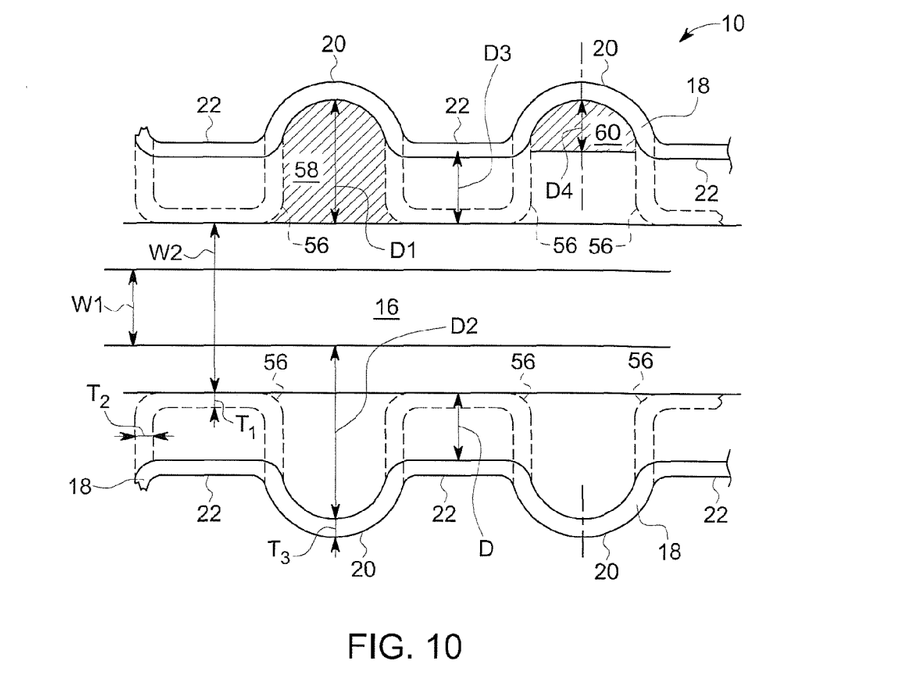
FIG. 10 is a diagrammatical illustration of an embodiment of a multiple lumen hose taken along line 10-10 in FIG. 1.

FIG. 10 is a diagrammatical illustration of a section of an exemplary embodiment of the multiple lumen hose 10 as shown in a sectional view taken along line 10-10 in FIG. 1.

The depiction of the multiple lumen hose 10 in FIG. 10 focuses on the base wall 18 in its corrugated form with a plurality of corrugations 20 as seen in FIG. 1, the sectional slice depicted in FIG. 10 is through the center of the scallop 22; however, for reference and the description herein, uncorrugated portions 56 of the base wall are depicted in dashed lines for reference purposes to show those areas that are not scalloped or corrugated.

The septum 16 extends between the base walls 18. It is to be understood that in some embodiments, the septum 16, and logically the initial dimensions of the integral co-extrusion, may be of an interior dimension smaller than that of the distance between the uncorrugated portions 56 of the multiple lumen hose 10. Such dimension is diagrammatically represented as distance W1 in FIG. 10. In an alternative embodiment, the integral co-extrusion is dimensioned such that the uncorrugated portions 56 are in effect the original dimensions of the integral co-extrusion as it enters the corrugator as described above. Such an embodiment is represented by reference dimension W2. It will be understood that alternative embodiments may vary between dimensions of W1 and W2. Dimension D1 depicts the distance that the septum 16 is stretched about the local region 58 (shaded) if the septum 16 has dimension W2 as in presently available multiple lumen hoses. If the septum 16 is smaller as represented by dimension W1, then the septum 16 must be stretched by exemplary dimension D2, which represents even greater stretching of the material.

As explained above, the process of corrugating stretches the plastic material of the base wall 18 outward to fill the molds of the corrugator. As the septum 16 is integrally connected to the base wall, the septum 16 also stretches to fill the corrugations 20. It is observed that the base wall 18 stretches to fill the molds, the base wall 18 thins. This results in the outermost areas of the corrugations being the thinnest. In FIG. 7, distance T1 represents the unstretched thickness of the base wall 18, which may be thickness in the order of 0.035 inches. Through a process of blow molding or vacuum forming or a combination of both, the molten plastic extruding resin stretches to fill the corrugations. Depending on the depth of the corrugations, exemplary distance D1, which may be 0.010 inches, the outside wall 18 at distance T3 may be as thin as 0.010 inches. This thinned area, juxtaposed against the reinforced area from the intersection of the base wall 18 with the septum 16, creates a localized stress concentration, which is susceptible to leaks.

In exemplary embodiments as set forth herein, the scallops 22 between each of the corrugations are disposed in a localized region about the septum 16. Particularly, the scallops 22 are located in the region wherein the septum 16 integrally intersects the base wall 1. In embodiments, the septum 16 is therefore already pre-stretched in the exemplary amount of dimension D3, such that when the corrugations 20 are formed, additional stretching the septum 16 is only required in the amount of dimension D4. This pre-stretching creates a much smaller local region 60 (shaded) of stretched lumen 16 to fill corrugation 20. It will be understood that the following dimensions are related in that D1=D3+D4. The effect of the pre-stretching in the amount of dimension D3 at the scallops 22 effectively spread any stretching of the septum 16 across the entire length of the multiple lumen hose 10 and therefore effectively reduces the localized region of stretching from area 58 down to area 60. By minimizing the local region of stretching 60, the applicants have discovered that the stretching results in improved septum integrity. Additionally, as the stretching of the septum 16 is spread out along the entire length of the multiple lumen hose 10, localized regions of extreme thinning of the septum 16 are reduced or eliminated, resulting in a more even surface across the septum 16. An even surface of septum 16 provides the further advantage of reduced resistance to gas or fluid flowing through the lumens defined by the septum. Furthermore and similarly, the outside wall 18, locally and with the addition of scallops 22, has only to stretch the distance D4 instead of D3. In the former example, this may result in an outside wall thinning down to 0.020 inches at distance T3 rather than 0.010 inches explained above. Although in some embodiments the thicker base wall 18 at dimension T3 may reduce flexibility in the axis with the septum 16, it has been observed that there is already limited flexibility in that direction, and a more durable corrugated hose is achieved.

FIG. 11 depicts a cross sectional view of an alternative embodiment of a dual lumen hose 80. The dual lumen hose 80 depicts a more extreme corrugation or difference between the interior diameter 82 of the base wall 84 and the interior diameter 86 of the corrugations 88. However, the embodiment of the dual lumen hose 80 still depicts similar relations between the structures as found in other embodiments. The circumferential base wall 84 extends at a radius 90 from a center point 92 aligned on the septum 94. The scallops 96 extend at a radius 98 that is smaller than radius 90. The radius 98 of the scallops 96 extend from center points 100 that are also aligned on the septum 94, but are different locations than the center point 92. The diameter between opposed interior sides of the scallops 96 is less than the interior diameter 86 of the corrugations. Thus, in exemplary embodiments wherein the scallops 96 are exemplarily circumferential, the relationship of the scallop radius 98 being smaller than base wall radius 90 and the diameter between opposed ends of the scallops 96 being less than the diameter of the corrugations provides a relationship between these dimensions in which the scallops are localized about the intersection of the septum 94 with the base wall 84.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A multiple lumen hose, the hose comprising:
    a generally circumferential base wall defining an interior;
    a plurality of corrugations extending radially outward from the base wall;
    a septum disposed interior to the base wall such as to divide the base wall into at least a first lumen and a second lumen, the septum secured to the circumferential base wall;
    a first scallop extending outward from the circumferential base wall between adjacent corrugations in a localized area about the septum, the septum secured to and extending into the first scallop; and
    a second scallop extending outward from the circumferential base wall between adjacent corrugations in a localized area about the septum, the septum secured to and extending into the second scallop.

2. The multiple lumen hose of claim 1, wherein the first and second scallops extend radially outward from respective center points aligned on the lumen and different from a center point of the circumferential base wall.

3. The multiple lumen hose of claim 1, wherein the plurality of corrugations extend radially past the first scallop and the second scallop.

4. The multiple lumen hose of claim 3, wherein the first scallop and the second scallop extend in a radial direction about half way between the circumferential base wall and the plurality of corrugations.

5. The multiple lumen hose of claim 1, wherein the first and second scallops reduce a distance that the septum and the corrugations are stretched.

6. The multiple lumen hose of claim 1, wherein a conduit is formed by vacuum molding an extrusion comprising the circumferential base wall and the septum.

7. The multiple lumen hose of claim 6, wherein the vacuum molding forms the first and second scallops and the corrugations by stretching the base wall and the septum.

8. The multiple lumen hose of claim 1, wherein the septum is dimensioned to extend between the opposed first and second scallops.

9. The multiple lumen hose of claim 1, wherein the scallops reduce the stretching of the corrugations at an intersection or with the septum.

10. The multiple lumen hose of claim 9, wherein the stretched septum is of a generally constant thickness.

\* \* \* \* \*